(12) United States Patent
Lapi

(10) Patent No.: US 8,790,283 B2
(45) Date of Patent: Jul. 29, 2014

(54) ASSISTING DEVICE FOR ADOPTING THE CORRECT POSTURE OF LOWER LIMBS AND FOR PURSUING WALKING ACTIVITY

(76) Inventor: Enrico Lapi, Santa Croce S/A (IT)

(*) Notice: Subject to any disclaimer, the term of this patent is extended or adjusted under 35 U.S.C. 154(b) by 971 days.

(21) Appl. No.: 12/936,123

(22) PCT Filed: Apr. 6, 2009

(86) PCT No.: PCT/IB2009/051438
§ 371 (c)(1),
(2), (4) Date: Oct. 1, 2010

(87) PCT Pub. No.: WO2009/125333
PCT Pub. Date: Oct. 15, 2009

(65) Prior Publication Data
US 2011/0034834 A1 Feb. 10, 2011

(30) Foreign Application Priority Data
Apr. 7, 2008 (IT) .................. PI2008A0028

(51) Int. Cl.
*A61H 1/00* (2006.01)
*A61H 1/02* (2006.01)
*A63B 21/02* (2006.01)

(52) U.S. Cl.
USPC ............ 601/35; 601/27; 601/33; 601/34; 482/124

(58) Field of Classification Search
USPC ........... 601/5, 23, 27–35; 602/23–25, 28–29, 602/32, 36; 482/122–126; 128/882
See application file for complete search history.

(56) References Cited

U.S. PATENT DOCUMENTS

| 1,015,054 | A | * | 1/1912 | McBride | 2/313 |
| 2,467,943 | A | * | 4/1949 | Mikell, Jr. | 482/79 |
| 2,514,870 | A | * | 7/1950 | Israel | 602/29 |
| 2,760,774 | A | * | 8/1956 | Perez | 482/79 |
| 2,815,021 | A | * | 12/1957 | Freeman | 602/24 |
| 4,249,523 | A | * | 2/1981 | Bidwell | 602/24 |
| 4,336,795 | A | | 6/1982 | Nichols | |
| 4,733,861 | A | * | 3/1988 | Plunkett, III | 482/126 |
| 4,736,946 | A | * | 4/1988 | Gordon | 482/125 |
| 4,815,731 | A | * | 3/1989 | Suarez et al. | 482/124 |
| 4,865,022 | A | * | 9/1989 | Gorsen | 602/33 |
| 4,955,370 | A | * | 9/1990 | Pettine | 602/28 |

(Continued)

FOREIGN PATENT DOCUMENTS

| DE | 20 2004 013 185 U1 | 4/2005 |
| FR | 2 877 834 | 5/2006 |
| GB | 2 274 591 A | 8/1994 |

*Primary Examiner* — Justine Yu
*Assistant Examiner* — Christopher Miller
(74) *Attorney, Agent, or Firm* — Johnson Legal PLLC

(57) ABSTRACT

A fitness/medical device assisting the movement of the lower limbs during the walking activity is substantially composed of brackets firmly connected to the shoes, a set of substantially rigid rods (7, 7A) connecting the brackets with articulation joints (6, 6A, 8, 8A, 9), elastic or inextensible cables for connecting the brackets, and at least one spring (5) acting between the rods and the connecting cables. The shape and joints of the various components of the kinematic mechanism allows accumulating the energy produced by one of the lower limbs when getting in contact with the ground, in order to give it back to the other lower limb when lifting from the ground, so producing a great reduction of the energy needed in the walking activity and at the same time promoting the acquisition of a correct posture.

10 Claims, 6 Drawing Sheets

(56) References Cited

U.S. PATENT DOCUMENTS

| | | | |
|---|---|---|---|
| 5,038,761 A | 8/1991 | Richardson | |
| 5,224,913 A * | 7/1993 | Rodibaugh | 482/124 |
| 5,318,494 A * | 6/1994 | Santighian | 482/125 |
| 5,336,151 A * | 8/1994 | Van Ballegooie | 482/124 |
| 5,569,135 A * | 10/1996 | Chen | 482/125 |
| 5,713,821 A * | 2/1998 | Nissen | 482/114 |
| 5,807,218 A * | 9/1998 | Nagatomo | 482/124 |
| 5,839,999 A * | 11/1998 | Pflugner | 482/140 |
| 6,036,665 A * | 3/2000 | Towsley | 602/23 |
| 6,368,256 B1 * | 4/2002 | Rumbaugh | 482/121 |
| 6,428,495 B1 * | 8/2002 | Lynott | 602/23 |
| 7,112,181 B1 * | 9/2006 | DeToro et al. | 602/27 |
| 7,150,248 B2 * | 12/2006 | Hodl | 119/818 |
| 7,931,571 B2 * | 4/2011 | Bernardoni | 482/124 |
| 2002/0068667 A1 * | 6/2002 | Strachan | 482/124 |
| 2003/0130098 A1 * | 7/2003 | Marco | 482/124 |
| 2006/0063651 A1 * | 3/2006 | Sload | 482/124 |
| 2007/0287616 A1 * | 12/2007 | Weaver | 482/124 |

* cited by examiner

ASSISTING DEVICE FOR ADOPTING THE CORRECT POSTURE OF LOWER LIMBS AND FOR PURSUING WALKING ACTIVITY

This Application is the National Stage of International Application No. PCT/IB2009/051438, international filing date of Apr. 6, 2009, which claims priority to IT Patent Application No. PI2008A000028, filed Apr. 7, 2008, the entire disclosures of which are incorporated herein by reference.

FIELD OF THE INVENTION

The present invention concerns a fitness and/or physiotherapy device for personal use, assisting to correctly make steps during the walking activity, assisting to regain functional capacity after pathology and also apt to allow better performances in the walking activity with lower energy consumption.

DESCRIPTION OF THE PRIOR ART

At present devices for improving effectiveness of the walking activity mainly concern tools aiming to improve a firm support of the foot on the ground, both during the impact phase and during the thrusting phase.

Such tools are usually elastic soles or shaped plantars inserted in the shoes and designed to promote a correct posture and to improve the walking performances.

Nevertheless the above tools, regardless of their construction quality, work by giving back the elastic power accumulated only to the limb where they are worn and according to a single resonant frequency, determined by the material of the specific tool, whilst they are not able to transfer said power to the opposite lower limb.

So, for this reason, they are not able to compensate little or great length differences of the limbs that may cause posture pathologies, nor they are able to optimize the recovery of the power spent in the walking activity in order to improve the performance and decrease the power consumption.

SUMMARY OF THE INVENTION

An object of the present invention is to avoid the above drawbacks of the prior art by providing an assisting device for correctly performing the walking activity able to use the force exerted by one lower limb when it gets in contact with the ground and the plantar bending begins in order to transmit said force to the opposite limb at the appropriate time and directions, so promoting a proper posture while walking.

A further object of the present invention is to propose an assisting device for correctly performing the walking activity, able to accumulate energy during the phase in which the foot gets in contact with the ground and the plantar bending begins for transmitting said energy to the opposite limb at the appropriate phase of the walking activity, improving this way the performance of the walking activity itself.

The above objects of the present invention are attained by means of a device, assisting the user in the walking activity apt to transfer forces from a lower limb to the other and also apt to promote a correct posture of the lower limbs during the walking activity, characterized in that it comprises: right and left fastening means for connecting to the right and left shoes, apt to create a substantially rigid connection between the soles of the shoes and the fastening means themselves; substantially rigid right and left rods connected together at one end by joints apt to stop at least translation degrees of freedom, and further connected to said fastening means at the other end by further joints apt to stop at least translation degrees of freedom; right and left leverage means connected together at one end by specific connection means and to the fastening means at the other end, the connection to the fastening means being obtained through hinge means apt to stop at least translation degrees of freedom and rotation about an axis transversally crossing the shoe to which the fastening means are bound; and further connection means for connecting said right and left rods to said connection means connecting said right and left leverage means.

Specific advantageous embodiments of the present invention are disclosed in the following where the kinematic mechanism formed by said rods, said leverage means, said connection means and the constraints thereof transfer, through said fastening means, the power produced by the lower limb that during the walking activity is getting in contact with the ground, to the opposite lower limb which is approaching the phase of lifting from the ground, said kinematic mechanism applying to the lower limbs forces apt to promote a correct posture of the lower limbs themselves and, in particular, of the feet.

BRIEF DESCRIPTION OF THE DRAWINGS

However, for a better understanding of the advantages and characteristics of the present invention, this will now be described by way of an embodiment example, with reference to the accompanying drawings, in which.

DETAILED DESCRIPTION OF PREFERRED EMBODIMENTS

Figure 1:
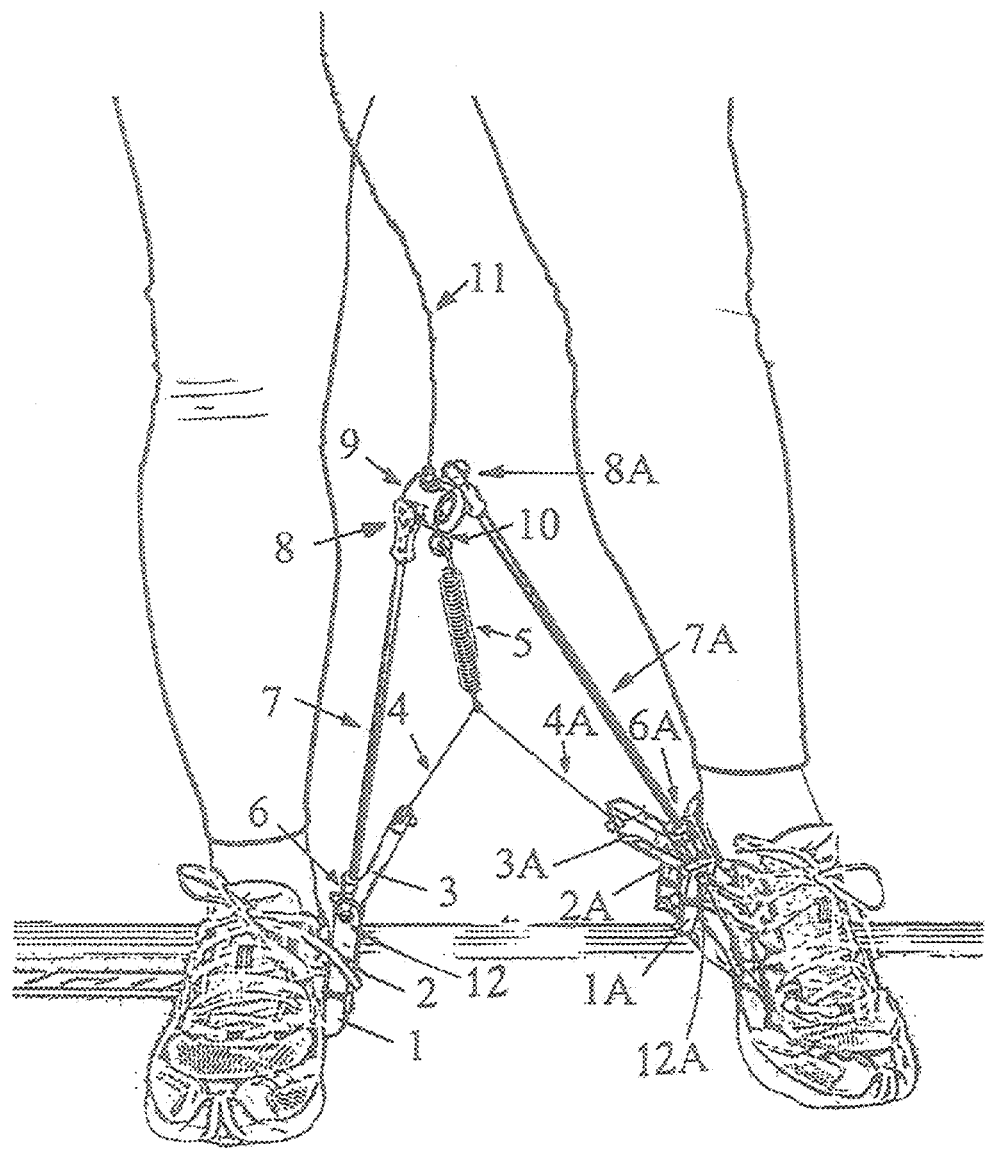
FIG. 1 shows a front view of a device according to the invention.
Figure 2:
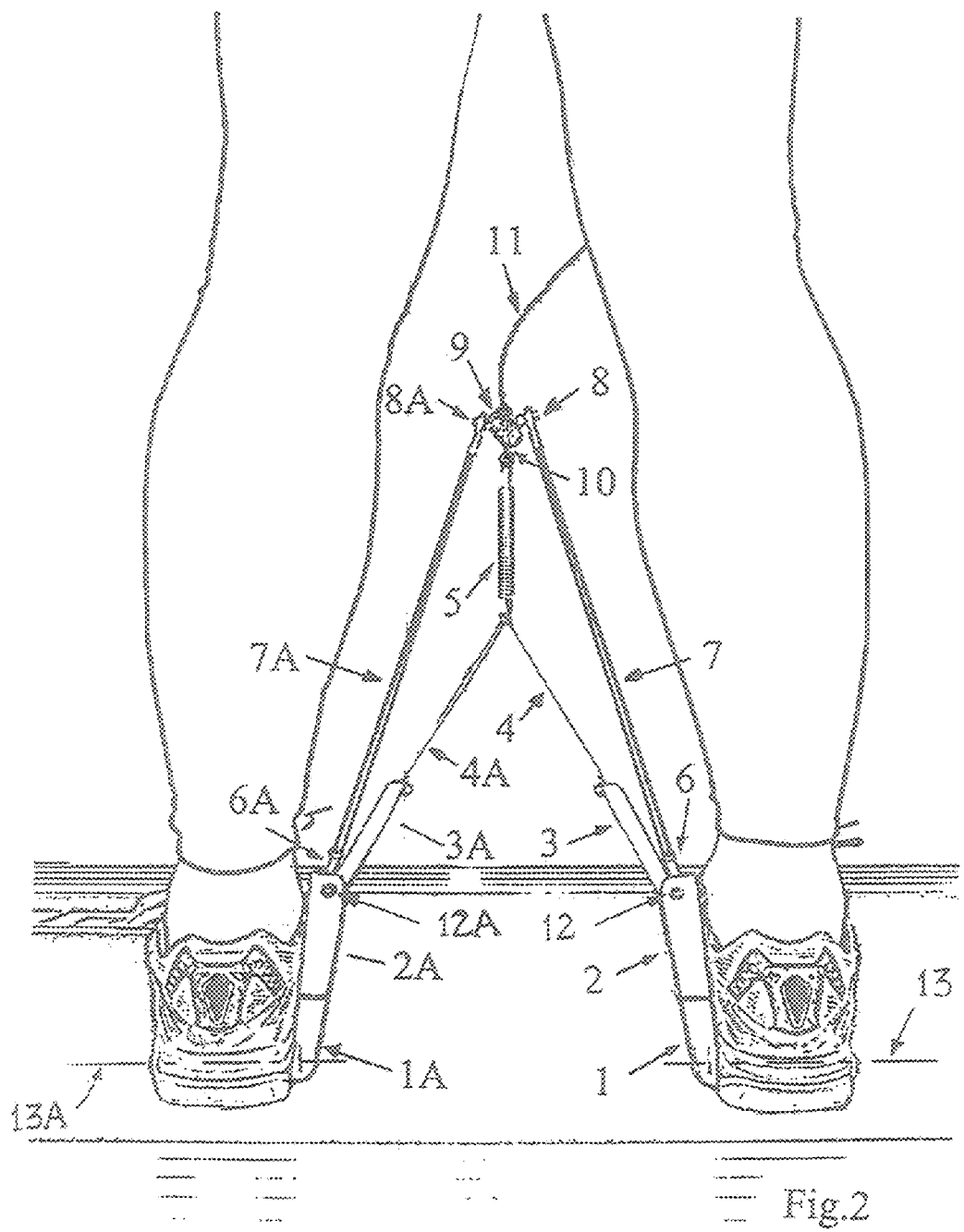
FIG. 2 shows a back view of the device of FIG. 1.

Referring to FIGS. 1 and 2 are schematically shown two brackets, 1 and 1A, rigidly bound to two standard shoes thanks to screw means transversally crossing the sole of the shoes.

To the brackets 1 and 1A are mounted two operation members, 2 and 2A, to which are bound, through a hinge having axis parallel to the longitudinal axis of the shoe, two levers, 3 and 3A, and to which are also bound through ball joints, 6 and 6A, two rods, 7 and 7A.

Once mounted together the bracket 1 and the operation member 2 thereof form the fastening means integral to the shoe to which they are bound. A similar rigid structure is formed at the opposite side by the left shoe, the bracket 1A and the operation member 2A.

The rods 7 and 7A have upper ends mutually connected in a way that allows articulation, the connection being obtained through two more ball joints, 8 and 8A, further connected to a center ball member, 9, so that the kinematic mechanism formed by the shoes, the fastening means 1, 1A, 2, 2A, the rods 7 and 7A and their connection member 9 is able to perform oscillation movements in a sagittal plane, opening out in a front plane, and more complex movements obtained from the combination of the above movements.

The levers 3 and 3A are connected together by two inextensible cables, 4 and 4A, that are further connected, at the other end, to a traction spring, 5, acting between said cables 4 and 4A and the center ball member 9.

A further cable, 10, connected to the spring 5, and sliding in a cable sheath, 11, allows the setting of the spring preload thanks to a ball-grip, not shown in the figures because it is of known techniques, which makes it possible to modify the action of the device according to the distinctive features of the user and according to the kind of utilization, by setting the hardness of the kinematic mechanism in order to obtain a synchronous mechanism oscillating together with the oscillation of the lower limbs or increasing the hardness to an amount that the power produced by one limb is directly transmitted to the opposite limb without accumulation of elastic potential energy in the elastic means of the device.

The overall view of FIG. 1 highlights that the lower limbs are able to adopt postures without any kind of limit imposed by the device.

The back view of FIG. 2 shows the symmetry of this embodiment in the sagittal plane.

Figure 3:
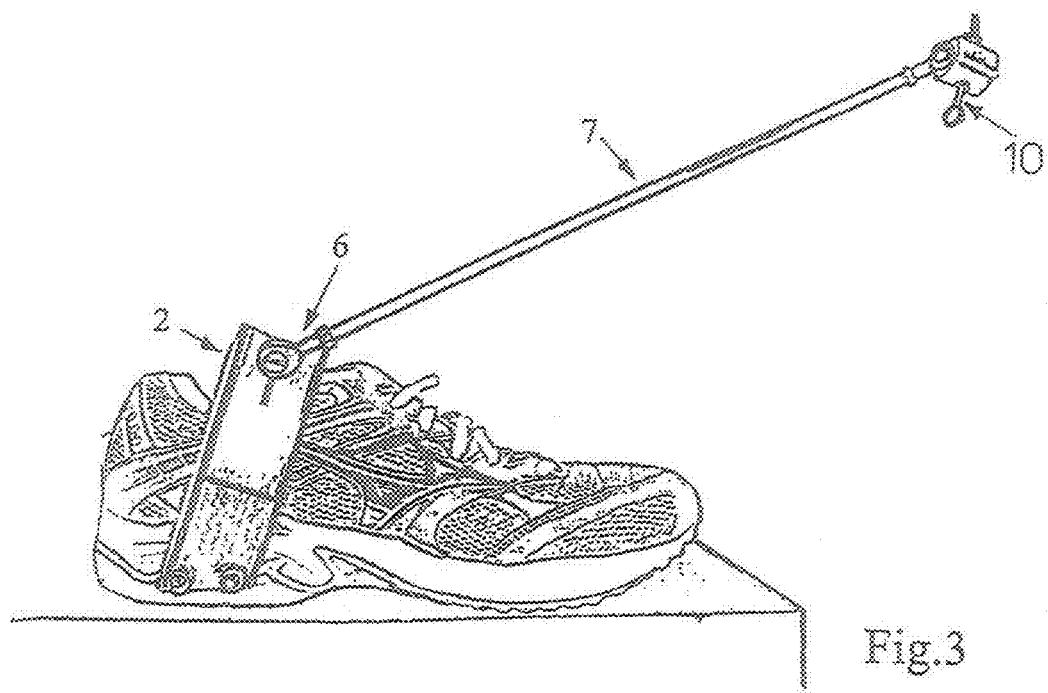
FIG. 3 shows side view of some components of the device of FIG. 1.

In FIG. 3 is shown the left half of the device where is visible the ball joint 6 connecting the operation member 2 with its rod 7 close to the left internal malleolus so underlining that every change of the angular position of the foot affects, through the shoe, the position of the operation member 2 that tends to change the angle that it forms with the rod and, vice versa, every change of the angle between rod and its operation member tend to cause, thanks to a combined action with the spring, a similar change in the shoe and the foot.

Figure 4:
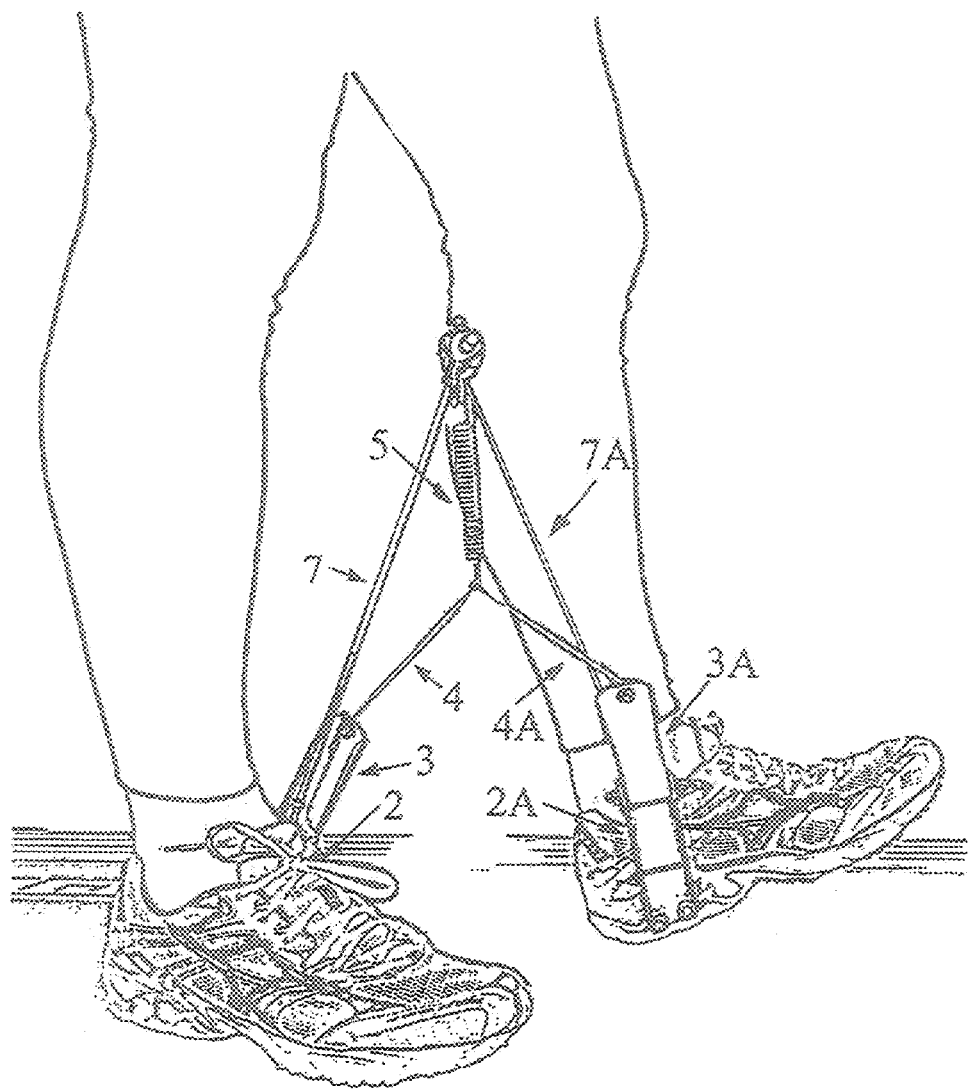
FIG. 4 shows a side view of the device of FIG. 1 during a specific working phase.

In the side view of FIG. 4 is shown the configuration of the device when the left limb gets in contact with the ground with transfer of load that produces plantar bending and changing of the angle between operation member 2A and rod 7A. The above change causes rising of the distance between the top end of the lever 3A, where is connected the cable 4A, and the center ball member 9, so producing stretching of the spring 5. The elastic force of the spring acts, through the system cable 4, lever 3 and fastening means 1 and 2, upon the opposite shoe and the foot. As easily intuitable such elastic force may cause lifting of the foot and plantar bending of the right foot, that are anyway prevented until a sufficient amount of body weight charges the limb and there is enough friction of the foot with the ground.

It has also to be noted that the angle, in the front plane, between the left operation member 2A and the hinged lever 3A produces an off-centre reaction force that tends to inwardly rotate the foot during the step loading phase, according to physiology data pointing out that during such phase of the walking activity an inward rotation of the hip occurs.

Figure 5:
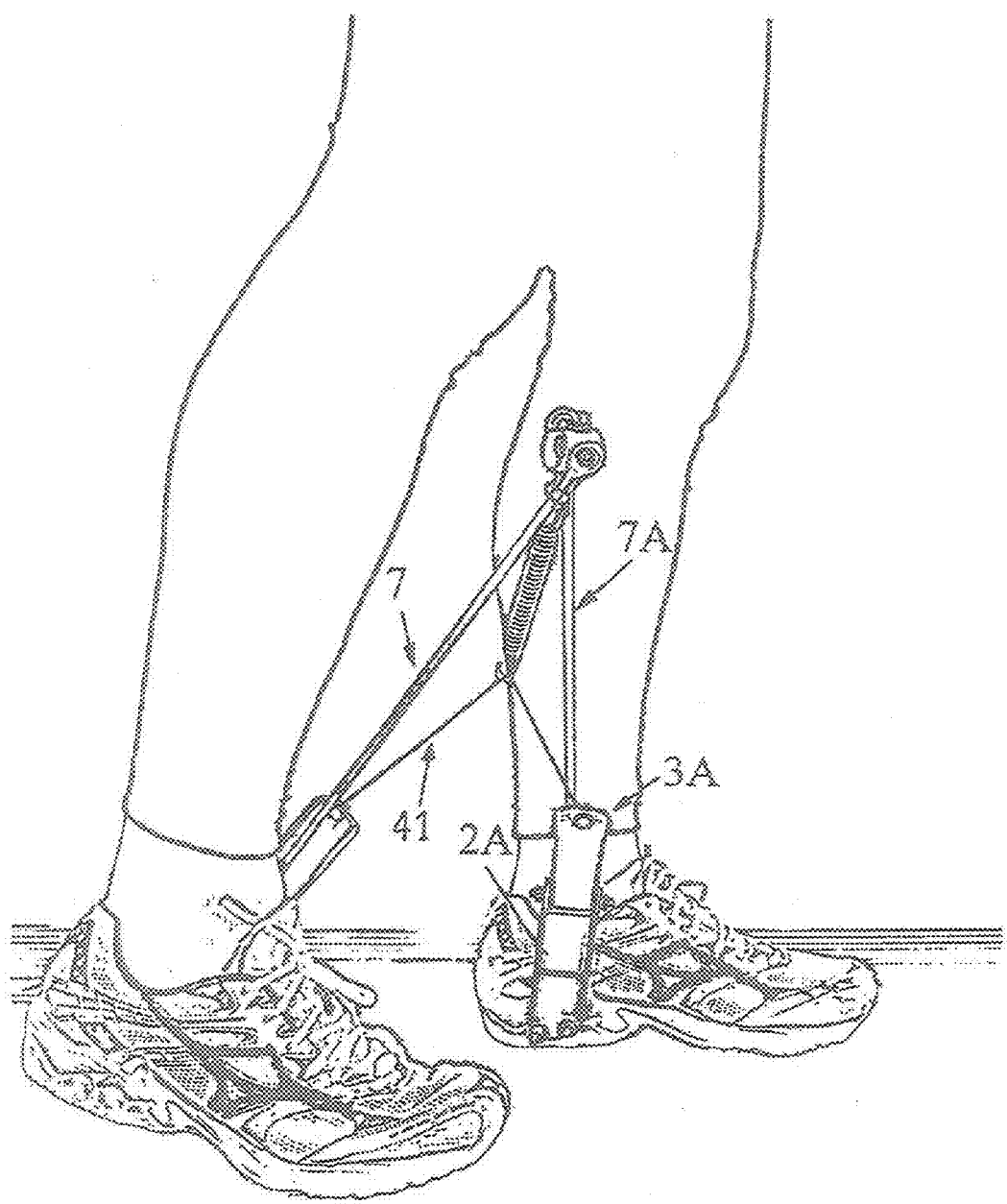
FIG. 5 shows a side view of the device of FIG. 4 during a different working phase.

In FIG. 5 is shown a subsequent phase of the step cycle, that is a subsequent working phase of the device according to the invention, in which the right limb, no more subject to the body weight, begins a complex movement of thrust and partial retrieval where plantar bending, knee bending and hip bending occur. Such complex movement is assisted by the elastic potential energy of the spring 5 that, acting through the cable 4 upon the lever 3, produces a reduction of the angle existing in the sagittal plane between the assembly formed by lever 3 and fastening means 1 and 2, with the rod 7, and also producing the alignment of this last with the opposite rod 7A. The angle between the right operation member 2 and the lever 3 induces also an outward rotation of the limb that also in this case matches with the physiology data pointing out that an outward rotation of the hip occurs during the pre-oscillation phase of the step, that is in the last phase of ground contact.

Figure 6:
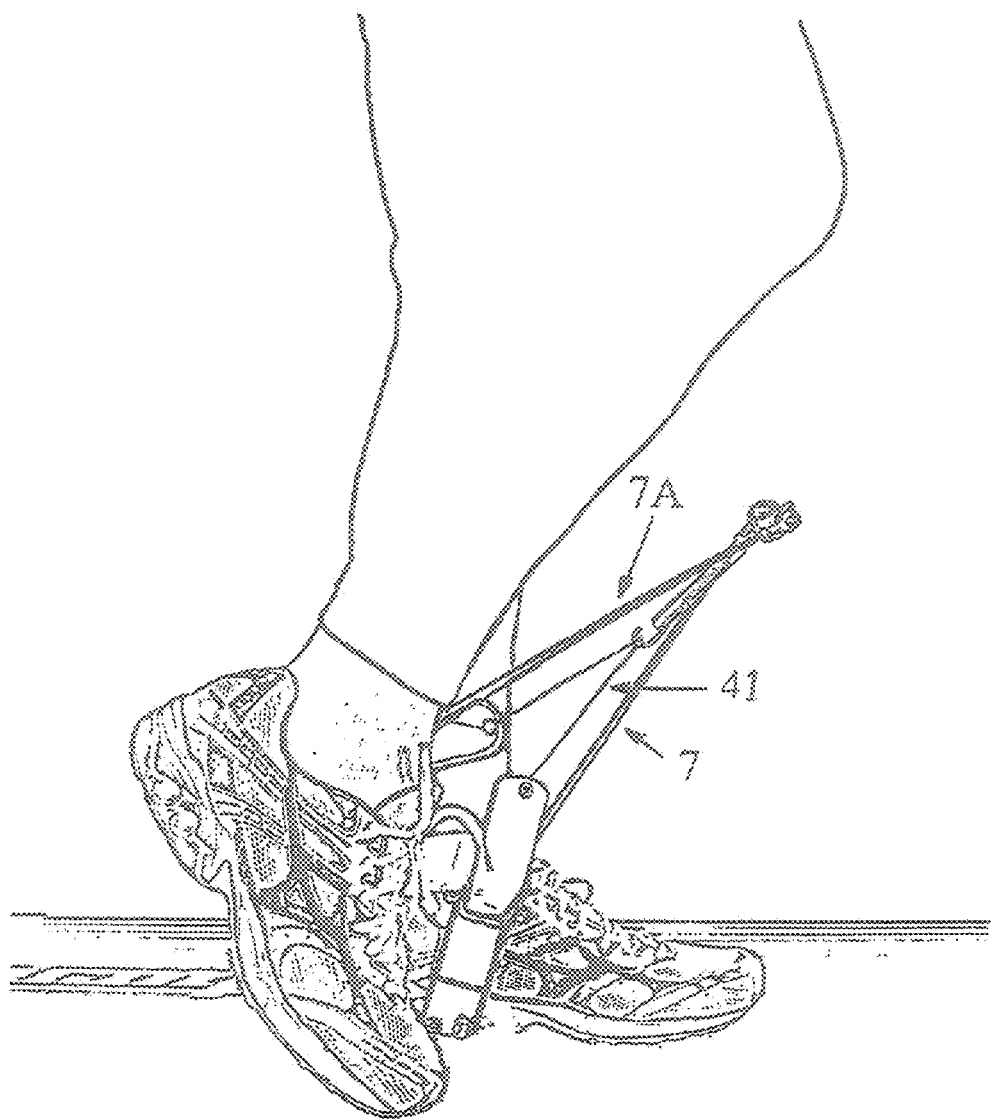
FIG. 6 shows a side view of the device of FIG. 4 during a further different working phase.

In FIG. 6 is shown a further phase of the step movement in which the retrieval of the right limb is completed, it loses contact with the ground and, after aligning with the opposite limb, it goes further toward a new contact with the ground. In this phase the rods 7 and 7A tend to align thanks to the remaining stretch of the spring after the foot lifting, so assisting the retrieval of the limb. In FIG. 6 has also to be noted that, thanks to the way the rods are jointed, the device is prevented from blocking during oscillation of the right limb as the rods tend to tilt toward the left foot touching the ground. At the end of this phase the step cycle starts again for the opposite limb.

The above disclosed device allows a consistent reduction of energy expense during the walking activity therefore increasing the performance of the user.

Furthermore the device assists at finding the correct and physiologic posture during said activity allowing a gradual and natural postural rehabilitation.

The possibility of setting the hardness of the mechanism allows also adapting the device to any kind of user as a function, in particular, of its weight and muscular strength.

The device is also very useful in case of specific pathologies or walking problems, such as, for instance, asymmetry of the lower limbs. In this case, in fact, after a physiology analysis, the right and left components of the device may be designed to be asymmetric in order to promote the removal of the lack of balance caused by the asymmetric limbs.

Certainly the above advantages remain even if changes or different embodiments of the invention are provided.

In fact, advantageously, the rods are made of carbon fiber which is a light and rigid material, but, to reduce costs or for production reasons, it is certainly possible to use different materials which are enough rigid and light like aluminium alloys or other materials. The shape of the rods, that in the disclosed embodiment are straight rods in order to reduce their costs, could vary, in case movements with large angles have to be allowed, and, if so, curved rods could be provided to avoid interference with the lower limbs.

Instead of the various ball joints could be used different joining means providing separate articulation for each perpendicular plane, as well as a ball joint could be combined with a joint allowing a single degree of freedom, in order to improve the movement capacity in a specific plane.

In particular, the mutual connection of the rods 7 and 7A could be obtained through a single ball joint, that could replace the two ball joints 8 and 8A and the center ball member 9, in order to simplify the structure of the device.

The joint corresponding to the tibia-tarsus articulation is placed at the side of the internal malleolus in order to reduce the complexity and the production costs, but, in case obstacles in this area have to be avoided, it can be placed at the side of the external malleolus, providing a curved rod able to connect to the opposite rod in the center sagittal plane in a way that interference with the lower limbs is prevented.

The way of fastening the device to the shoes could be obviously different, for instance by using specific sole to be housed in the shoe, or even by realizing special shoes directly comprising brackets 1, 1A.

The ball joints and the joints of the spring 5 too could be provided with setting mechanisms so that the hardness of the various components and articulations of the device may be adjusted to fit the needs and size of different users, as well as specifically sized versions of the device could be realized on demand.

The ability of accumulating energy that in the disclosed embodiment is attained thanks to the spring 5 could be attained in a different way. In addition, for specific requirements, one or both the cables 4 and 4A could be replaced by elastic means 41, and/or the spring 5 could be replaced by an inextensible cable.

Obviously the spring 5 could be replaced by elastic means of a different type.

The spring setting mechanism made with a ball-grip allows a soft regulation but a more rapid mechanism, such as a lever or an automatic system, may be provided.

Finally, a damping mechanism is not provided in the embodiment but, in case it would be suitable, dampers could be mounted at the joints or along the cables.

These and more modifications may be carried out, anyway, within the ambit of protection of the following claims

The invention claimed is:

1. A device for assisting a user in a walking activity, wherein the device is configured to transfer forces from a lower limb to an other lower limb and promote a correct posture of the lower limbs during the walking activity, comprising:
    right and left fastening means (1, 2, 1A, 2A) for connecting to right and left shoes, respectively, configured to create a substantially rigid connection to the soles of the shoes;
    substantially rigid right and left rods (7, 7A) connected together at one end by first joints (8, 8A, 9) configured to stop at least translation degrees of freedom, and further connected to said fastening means (1, 2, 1A, 2A) at an other end by second joints (6, 6A) configured to stop at least translation degrees of freedom;
    right and left leverage means (3, 3A) connected together at one end by connection means (4, 4A) and to the fastening means (1, 2, 1A, 2A) at an other end, the connection to the fastening means being obtained through hinge means (12, 12A) configured to stop at least translation degrees of freedom and rotation about an axis (13, 13A) transversally crossing the shoe to which the fastening means are bound; and
    a spring (5) for connecting said right and left rods (7, 7A) to said connection means (4, 4A) connecting said right and left leverage means (3, 3A).

2. The device according to claim 1, wherein said first joints (8, 8A, 9) comprise ball joints (8, 8A) and said second joints (6, 6A) comprise ball joints.

3. The device according to claim 1, wherein said right and left fastening means (1, 2, 1A, 2A) comprise brackets (1, 1A) bound to the shoes.

4. The device according to claim 1, wherein said right and left rods (7, 7A) are straight rods.

5. The device according to claim 1, wherein said right and left leverage means (3, 3A) are connected together by flexible substantially inextensible connection means (4, 4A).

6. The device according to claim 1, wherein said leverage means (3, 3A) are connected together by flexible elastic connection means (41).

7. The device according to claim 1, further comprising a setting means configured to regulate a preload hardness of said spring (5),
    said setting means comprising a cable (10) connected to said spring (5), a cable sheath (11) and a ball-grip, said cable (10) passing through said cable sheath (11) having length sufficient to house said ball-grip at a user's belt or pocket.

8. The device according to claim 1, wherein said fastening means (1, 2, 1A, 2A) comprise:
    brackets (1, 1A) firmly connected to the shoes; and
    operation members (2, 2A) connected to said rods (7, 7A) and to said leverage means (3, 3A);
    said brackets being connected to said operation members.

9. The device according to claim 1, wherein a kinematic mechanism formed by said right and left rods (7, 7A), said right and left leverage means (3, 3A), said connection means (4, 4A), said spring (5), said first joints (8, 8A, 9) and second joints (6, 6A) are configured to transfer a power produced by the lower limb to the other lower limb through said fastening means (1, 2, 1A, 2A), wherein said power is produced by the lower limb during a step phase in which the shoe is in contact with the ground, while the other lower limb is lifting off of the ground, wherein said kinematic mechanism is configured to apply forces on said lower limbs configured to promote a correct posture of the lower limbs themselves, and of the feet thereof.

10. A device for assisting a user in a walking activity, wherein the device is configured to transfer forces from a lower limb to an other lower limb and promote a correct posture of the lower limbs during the walking activity, comprising:
    right and left fastening means (1, 2, 1A, 2A) for connecting to right and left shoes, respectively, configured to create a substantially rigid connection to soles of the shoes;
    substantially rigid right and left rods (7, 7A) connected together at one end by first joints (8, 8A, 9) configured to stop at least translation degrees of freedom, and further connected to said fastening means (1, 2, 1A, 2A) at an other end by second joints (6) configured to stop at least translation degrees of freedom;
    right and left leverage means (3, 3A) connected together at one end by flexible elastic connection means (41) and to the fastening means (1, 2, 1A, 2A) at an other end, the connection to the fastening means being obtained through hinge means configured to stop at least translation degrees of freedom and rotation about an axis transversally crossing the shoe to which the fastening means are bound; and
    an inextensible cable for connecting said right and left rods (7, 7A) to said connection means (4, 4A) connecting said right and left leverage means (3, 3A).

* * * * *